(12) United States Patent
Fenech et al.

(10) Patent No.: US 10,729,886 B2
(45) Date of Patent: Aug. 4, 2020

(54) AXIAL SUPPORT STRUCTURE FOR A FLEXIBLE ELONGATE DEVICE

(71) Applicant: INTUITIVE SURGICAL OPERATIONS, INC., Sunnyvale, CA (US)

(72) Inventors: Carolyn M. Fenech, San Jose, CA (US); Hans F. Valencia, Santa Clara, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 245 days.

(21) Appl. No.: 15/685,979

(22) Filed: Aug. 24, 2017

(65) Prior Publication Data

US 2018/0056040 A1    Mar. 1, 2018

Related U.S. Application Data

(60) Provisional application No. 62/378,943, filed on Aug. 24, 2016, provisional application No. 62/535,673, filed on Jul. 21, 2017.

(51) Int. Cl.
*A61M 25/01* (2006.01)
*A61M 25/00* (2006.01)
(Continued)

(52) U.S. Cl.
CPC ....... *A61M 25/0152* (2013.01); *A61B 1/0011* (2013.01); *A61B 1/0016* (2013.01);
(Continued)

(58) Field of Classification Search
CPC ........ A61B 1/0055; A61B 2017/00314; A61B 1/008
See application file for complete search history.

(56) References Cited

U.S. PATENT DOCUMENTS 6,380,732 B1    4/2002  Gilboa
6,389,187 B1    5/2002  Greenaway et al.
(Continued)

FOREIGN PATENT DOCUMENTS

EP    1690564 A1    8/2006

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
(Continued)

*Primary Examiner* — Nathan R Price
*Assistant Examiner* — Anh Bui
(74) *Attorney, Agent, or Firm* — Haynes and Boone, LLP

(57) ABSTRACT

An axial support structure for a flexible elongate device includes a plurality of rigid links. each link comprises a shaft, a pair of male joint connectors comprising a male tab coplanar with the shaft extending from a first end, and a pair of female joint connectors comprising a female tab coplanar with the shaft extending from a second end. Each of the male joint connectors includes a pin extending from the male tab in a direction perpendicular to an axial direction of the shaft and each female tab defines an aperture. Each of the plurality of rigid links is rotated by 90 degrees with respect to neighboring links among the plurality of rigid links, thereby aligning each pair of male joint connectors with a neighboring pair of female joint connectors to form pin joints in which each aperture encircles a corresponding pin.

12 Claims, 8 Drawing Sheets

(51) Int. Cl.
  *A61B 34/35*   (2016.01)
  *A61B 34/37*   (2016.01)
  *A61B 90/00*   (2016.01)
  *A61B 34/20*   (2016.01)
  *A61B 1/00*    (2006.01)
  *A61B 1/005*   (2006.01)
  *A61B 1/267*   (2006.01)
  *A61B 34/30*   (2016.01)
  *A61B 17/00*   (2006.01)

(52) U.S. Cl.
  CPC ............ *A61B 1/0055* (2013.01); *A61B 34/20* (2016.02); *A61B 34/35* (2016.02); *A61B 34/37* (2016.02); *A61B 90/37* (2016.02); *A61M 25/0012* (2013.01); *A61M 25/0026* (2013.01); *A61M 25/0045* (2013.01); *A61M 25/0138* (2013.01); *A61B 1/00128* (2013.01); *A61B 1/2676* (2013.01); *A61B 2017/00314* (2013.01); *A61B 2017/00323* (2013.01); *A61B 2034/2051* (2016.02); *A61B 2034/2055* (2016.02); *A61B 2034/2059* (2016.02); *A61B 2034/2061* (2016.02); *A61B 2034/301* (2016.02); *A61B 2090/365* (2016.02); *A61B 2090/3614* (2016.02); *A61B 2090/371* (2016.02); *A61B 2090/374* (2016.02); *A61B 2090/376* (2016.02); *A61B 2090/3735* (2016.02); *A61B 2090/3762* (2016.02); *A61M 25/0009* (2013.01); *A61M 25/0147* (2013.01); *A61M 2025/0037* (2013.01)

(56) References Cited

U.S. PATENT DOCUMENTS

| | | | |
|---|---|---|---|
| 6,450,948 B1 | 9/2002 | Matsuura et al. | |
| 6,623,448 B2 | 9/2003 | Slater | |
| 7,772,541 B2 | 8/2010 | Froggatt et al. | |
| 7,781,724 B2 | 8/2010 | Childers et al. | |
| 8,900,131 B2 | 12/2014 | Chopra et al. | |
| 2003/0097128 A1 | 5/2003 | Hayzelden | |
| 2005/0272978 A1* | 12/2005 | Brunnen | A61B 1/0011 600/142 |
| 2006/0013523 A1 | 1/2006 | Childlers et al. | |
| 2007/0161857 A1 | 7/2007 | Durant et al. | |
| 2007/0161860 A1* | 7/2007 | Hosoi | A61B 1/005 600/142 |
| 2009/0062606 A1 | 3/2009 | Ueda et al. | |
| 2009/0099420 A1 | 4/2009 | Woodley et al. | |
| 2009/0182200 A1 | 7/2009 | Golden et al. | |
| 2009/0192495 A1* | 7/2009 | Ostrovsky | A61B 1/0055 604/528 |
| 2009/0242115 A1* | 10/2009 | Ito | A61B 1/0011 156/293 |
| 2011/0004157 A1 | 1/2011 | Dewaele et al. | |
| 2011/0015648 A1* | 1/2011 | Alvarez | A61B 17/221 606/130 |
| 2011/0237888 A1 | 9/2011 | Matsushita | |
| 2011/0306836 A1 | 12/2011 | Ohline et al. | |
| 2013/0096377 A1 | 4/2013 | Duindam et al. | |
| 2013/0096385 A1 | 4/2013 | Fenech et al. | |
| 2013/0274784 A1 | 10/2013 | Lenker et al. | |
| 2017/0156567 A1 | 6/2017 | Kaneko | |

OTHER PUBLICATIONS

Extended European Search Report for Application No. 14856191.3, dated Apr. 7, 2017, 10 pages.
International Preliminary Report on Patentability for Application No. PCT/US14/62160, dated May 6, 2016, 13 pages.
International Preliminary Report on Patentability for Application No. PCT/US2014/062188, dated May 6, 2016, 12 pages.
International Search Report and Written Opinion for Application No. PCT/US14/62160, dated Jan. 28, 2015, 16 pages.
International Search Report and Written Opinion for Application No. PCT/US14/62188, dated Feb. 4, 2015, 15 pages.
Extended European Search Report for Application No. 14855614.5, dated Apr. 7, 2017, 9 pages.

* cited by examiner

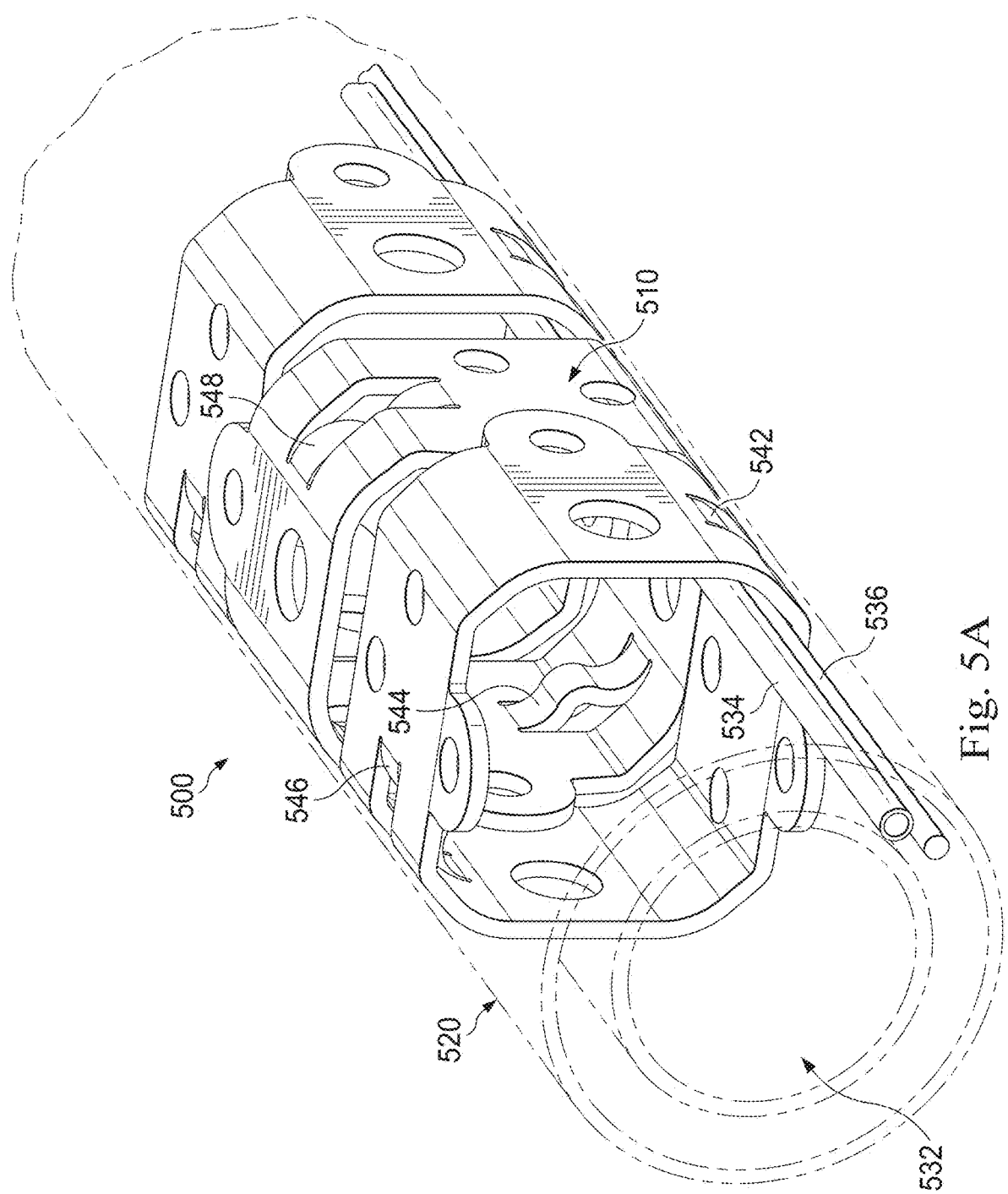

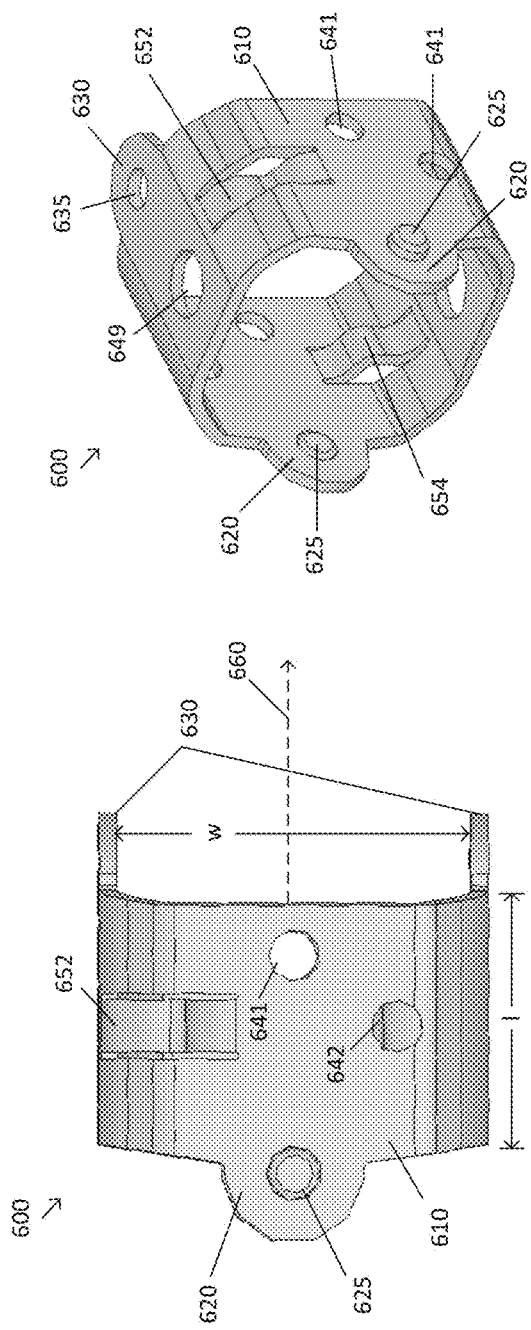
FIG. 6A
FIG. 6B
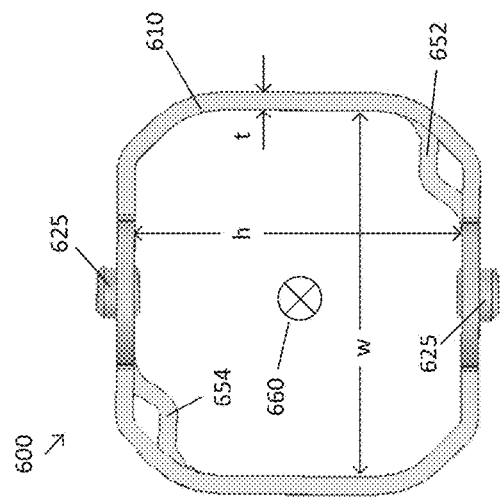
FIG. 6D
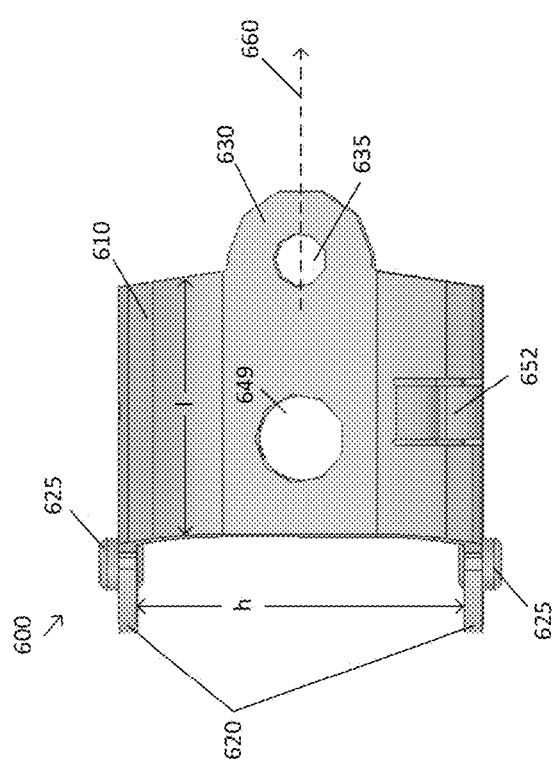
FIG. 6C

AXIAL SUPPORT STRUCTURE FOR A FLEXIBLE ELONGATE DEVICE

RELATED APPLICATIONS

This patent application claims priority to and the benefit of the filing date of U.S. Provisional Patent Application No. 62/378,943 entitled "Axial Support Structure for a Flexible Elongate Device," filed Aug. 24, 2016, and U.S. Provisional Patent Application No. 62/535,673 entitled "Flexible Elongate Devices and Methods," filed Jul. 21, 2017.

TECHNICAL FIELD

The present disclosure is directed to a support structure for an elongate device and more particularly to a linked axial support structure for a flexible elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. In some applications, the flexible and/or steerable elongate device is subjected to axial loads during operation (e.g., pulling and/or pushing forces along an axial direction of the elongate device). If the axial loads exceed the axial strength of the elongate device, the elongate device and/or medical instruments may be damaged and the patient may be injured.

Accordingly, it would be advantageous to provide axial support structures for flexible and/or steerable elongate devices, such as steerable catheters, that are suitable for use during minimally invasive medical techniques.

SUMMARY

The embodiments of the invention are best summarized by the claims that follow the description.

In some embodiments, an axial support structure for a flexible elongate device includes a plurality of rigid links coupled by pin joints. Each of the plurality of rigid links comprises a shaft, a pair of male joint connectors extending axially from a first end of the shaft, and a pair of female joint connectors extending axially from a second end of the shaft opposite the first end. The female joint connectors are complementary to the male joint connectors and are rotated by 90 degrees relative to the male joint connectors. Each of the plurality of rigid links is rotated by 90 degrees with respect to neighboring links among the plurality of rigid links, thereby aligning each pair of male joint connectors with a neighboring pair of female joint connectors to form the pin joints.

In some embodiments, an axially reinforced flexible body includes a pliable tube and an axial support structure disposed within the pliable tube. The axial support structure includes a plurality of rigid links coupled by pin joints. Each of the plurality of rigid links includes a shaft, a set of male joint connectors extending in an axial direction from a first end of the shaft, and a set of female joint connectors extending in the axial direction from a second end of the shaft opposite the first end. The set of female joint connectors are complementary to the set of male joint connectors and are rotated by 90 degrees relative to the set of male joint connectors. Each of the plurality of rigid links is rotated by 90 degrees with respect to neighboring links among the plurality of rigid links, thereby aligning each set of male joint connectors with a neighboring set of female joint connectors to form the pin joints.

In some embodiments, a method for fabricating an axially reinforced flexible body includes forming a plurality of rigid links, coupling the plurality of rigid links to form an axial support structure, and encapsulating the axial support structure in a pliable tube to form an axially reinforced flexible body. Each of the plurality of rigid links includes a shaft, a set of male joint connectors extending axially from a first end of the shaft, and a set of female joint connectors extending axially from a second end of the shaft opposite the first end. The set of female joint connectors are complementary to the set of male joint connectors and are rotated by 90 degrees relative to the set of male joint connectors. Each of the plurality of rigid links is rotated by 90 degrees with respect to neighboring links among the plurality of rigid links, thereby aligning each set of male joint connectors with a neighboring set of female joint connectors to form pin joints.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIGS. 5A and 5B are simplified diagrams of an axially reinforced flexible body according to some embodiments.

FIGS. 6A-D are simplified diagrams of a rigid link for an axial support structure according to some embodiments.

Figure 7:
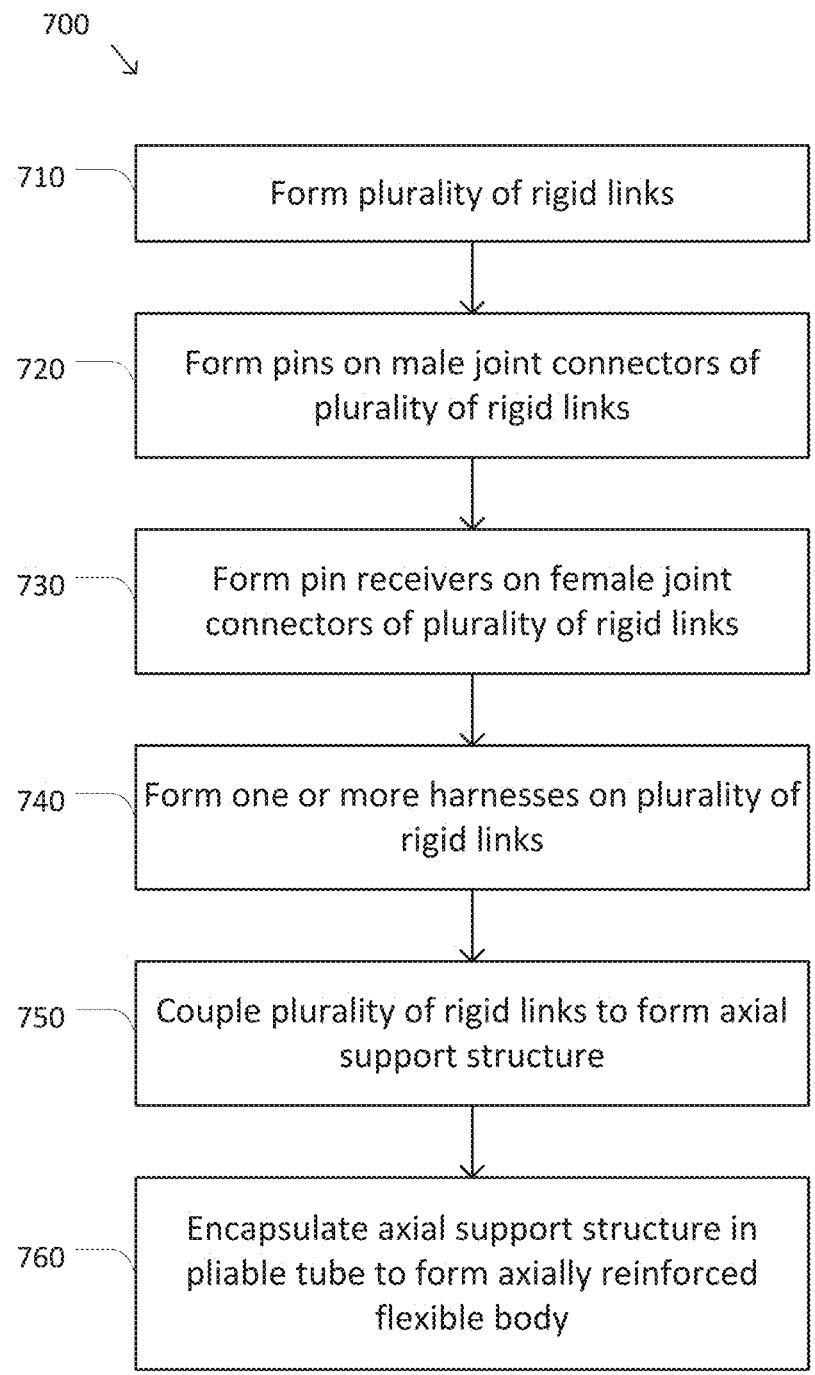

FIG. 7 is a simplified diagram of a method for fabricating an axially reinforced flexible body according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
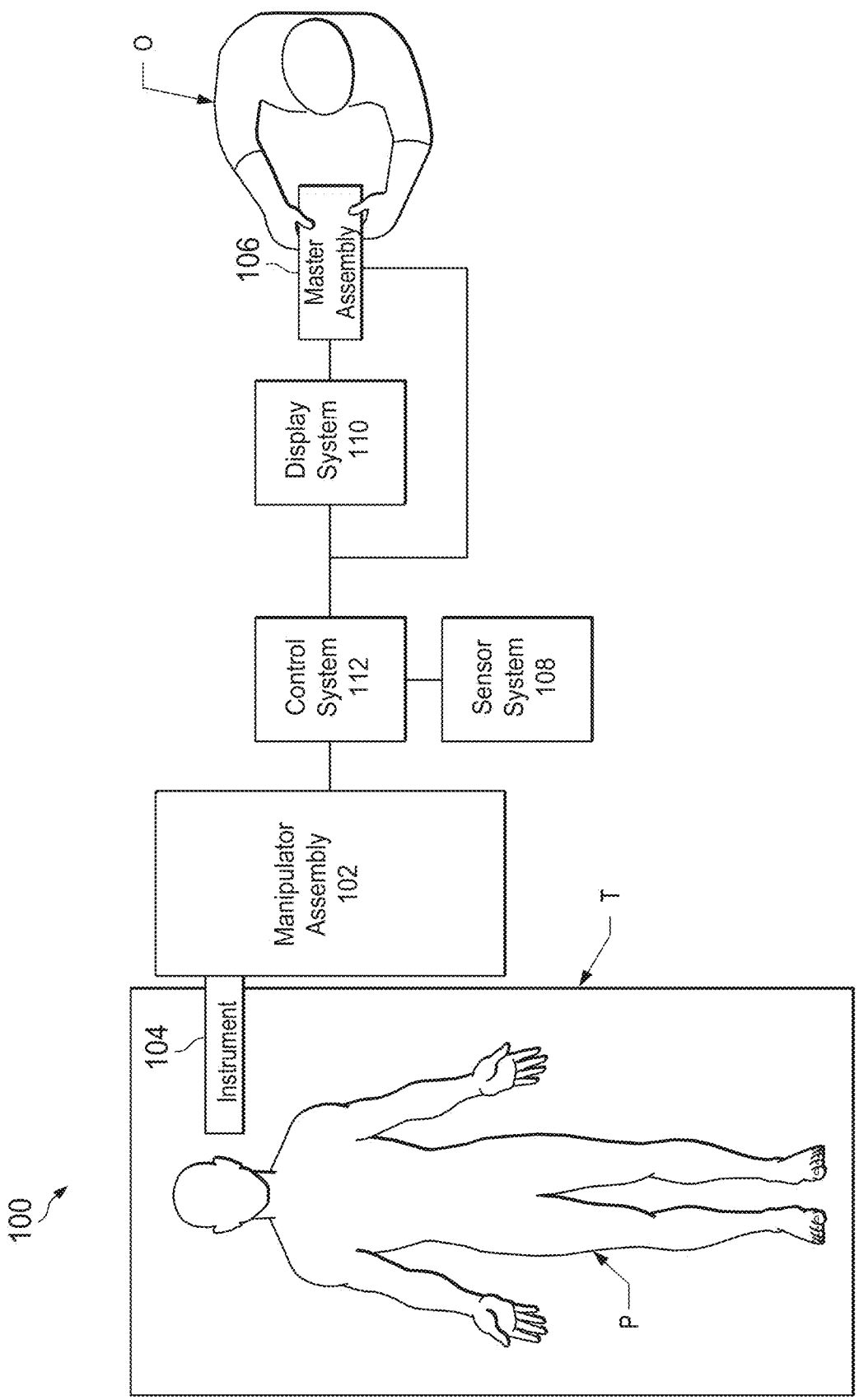
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a physician's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MM), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
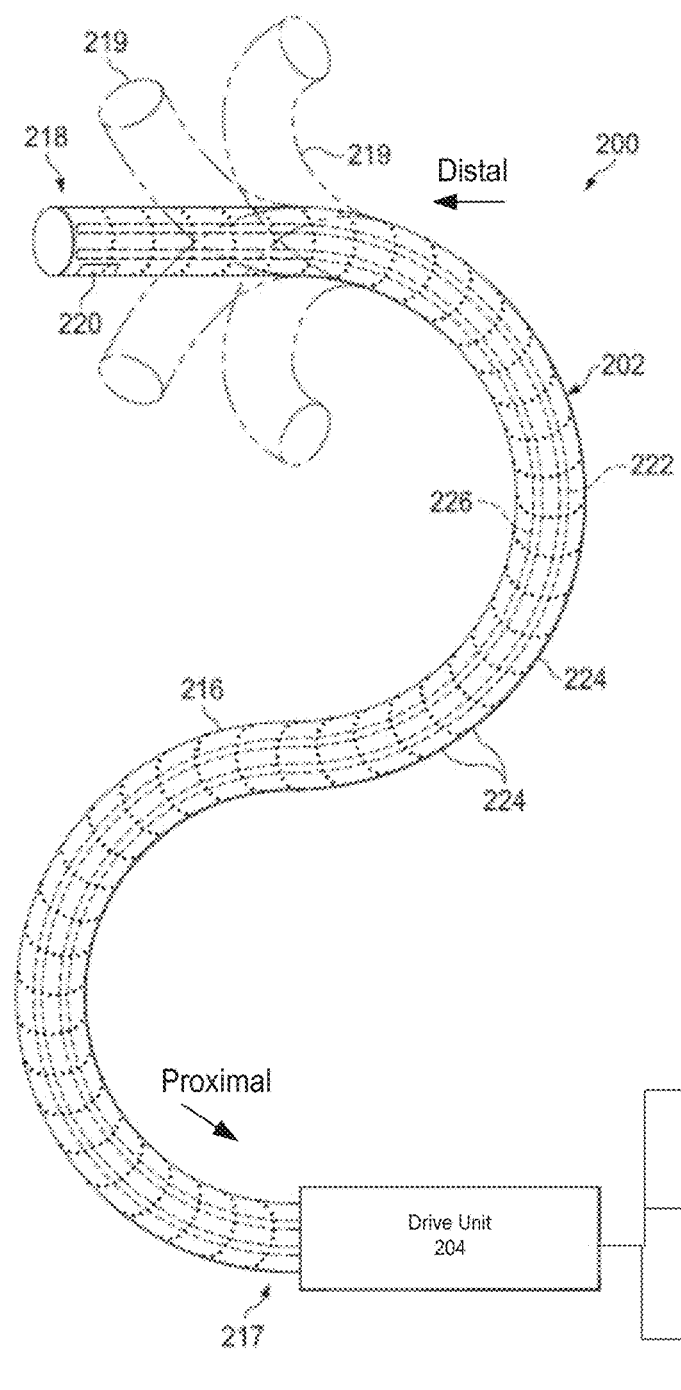
FIG. 2A is a simplified diagram of a medical instrument system according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202 coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of flexible body 216 at distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of flexible body 216 may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
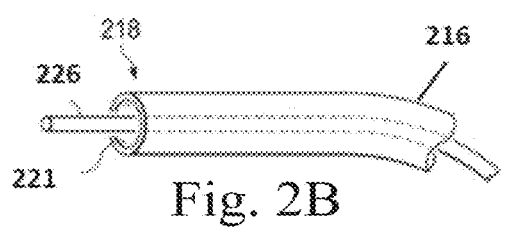
FIG. 2B is a simplified diagram of a medical instrument with an extended medical tool according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician, clinician, or surgeon or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
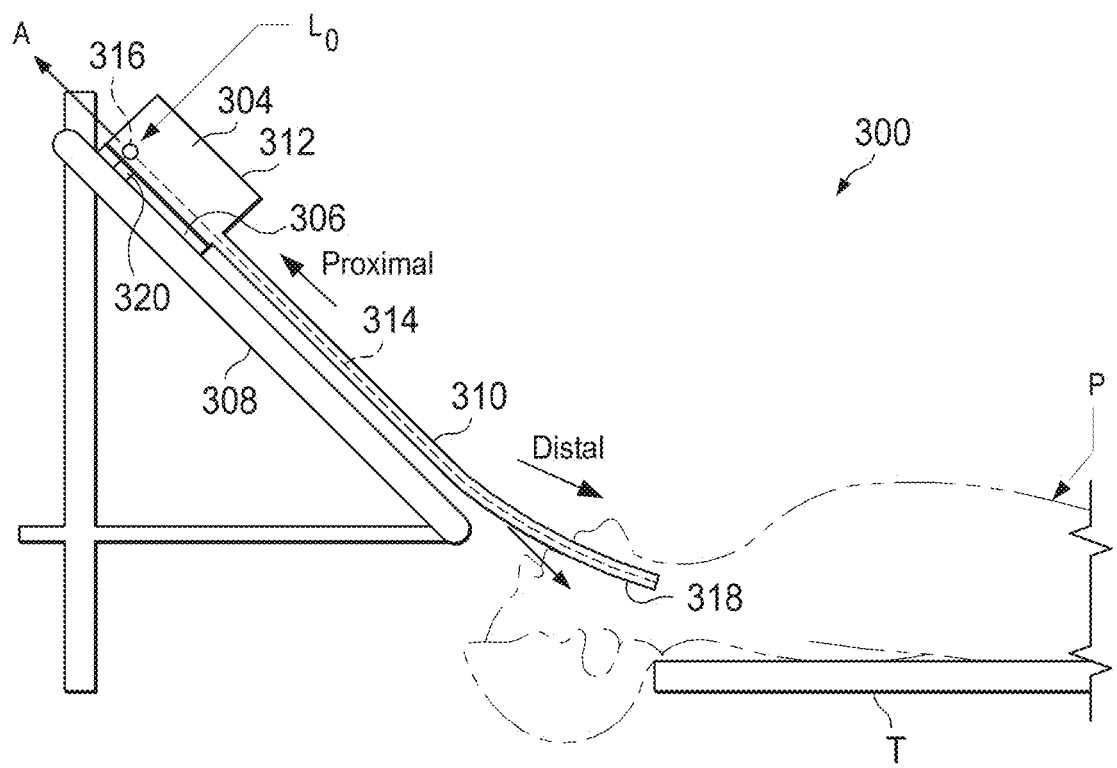
FIGS. 3A and 3B are simplified diagrams of side views of a patient coordinate space including a medical instrument mounted on an insertion assembly according to some embodiments.
Figure 3B:
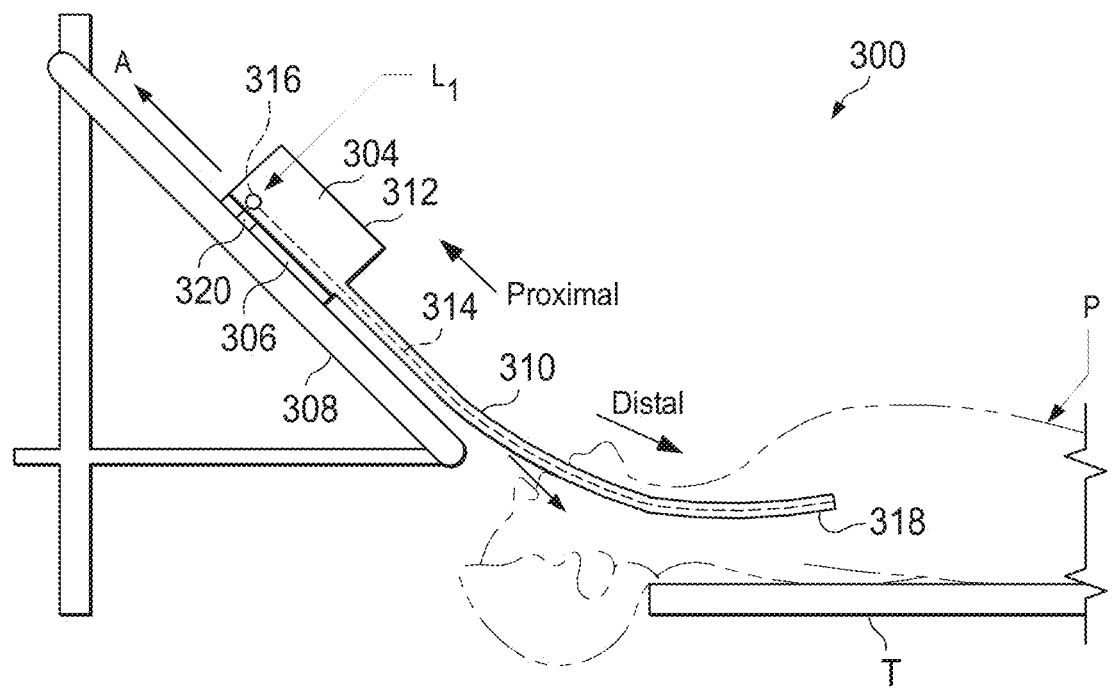

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position LX may further be used as an indicator of the distance or insertion depth to which distal end 318 of elongate device 310 is inserted into the passageways of the anatomy of patient P.

Figure 4:
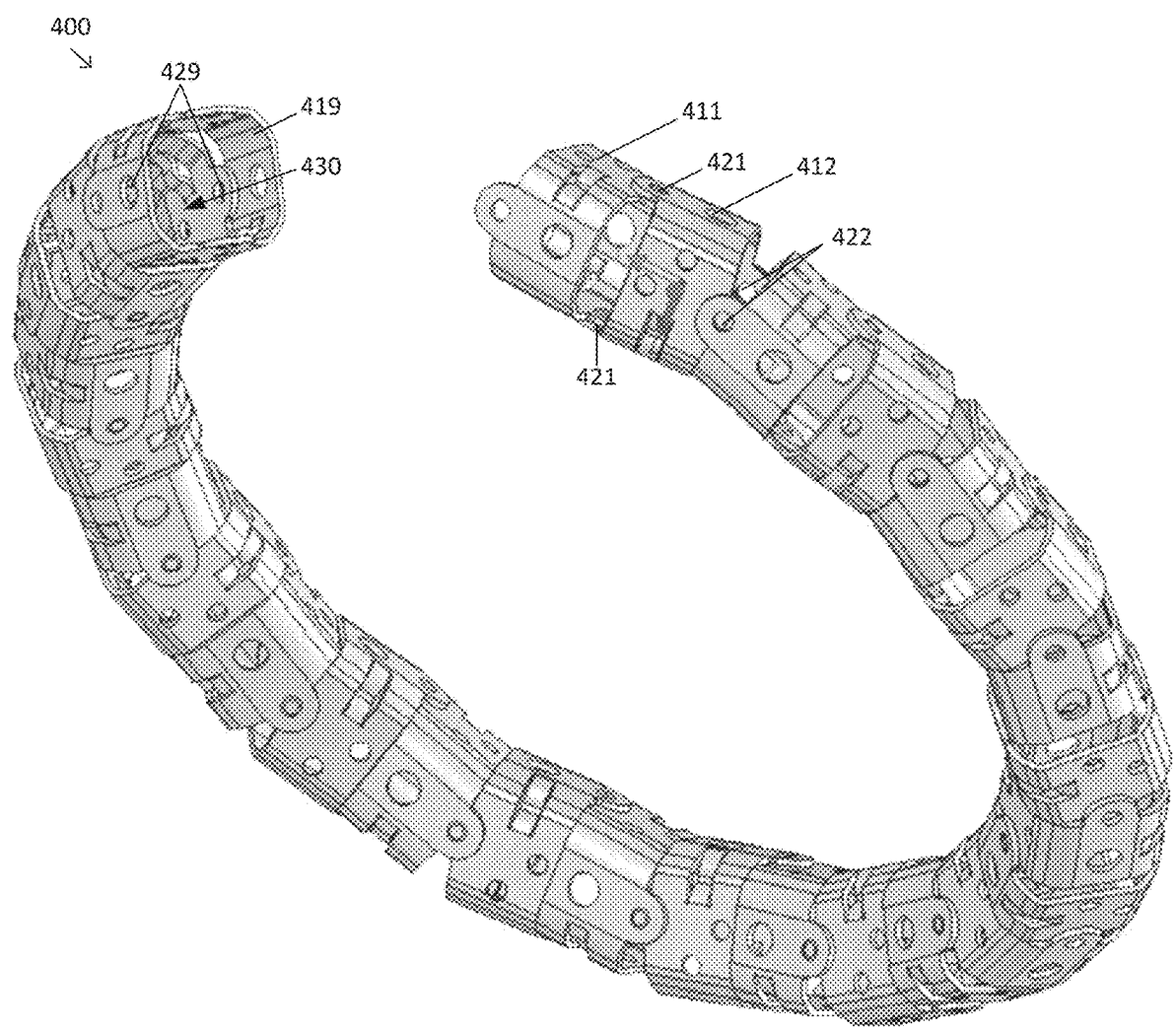
FIG. 4 is a simplified diagram of an axial support structure according to some embodiments.

FIG. 4 is a simplified diagram of an axial support structure 400 according to some embodiments. According to some embodiments consistent with FIGS. 1-3, axial support structure 400 may be incorporated into a flexible elongate device, such as elongate device 202 and/or flexible body 216. According to some embodiments, axial support structure 400 may be incorporated into a steerable portion of the flexible elongate device. For example, the steerable portion of the flexible elongate device may be controlled using one or more pull wires that generate axial loads on the flexible elongate device during operation. Consistent with such embodiments, axial support structure 400 may support the flexible elongate device against the axial loads generated by the one or more pull wires. In particular, axial support structure 400 may prevent or reduce distortion, compression and/or collapse of the flexible elongate device while retaining its flexibility and/or steerability.

Axial support structure 400 is composed of a plurality of rigid links 411-419. Rigid links 411-419 are coupled to each other by pin joints 421-429. According to some embodiments, each of rigid links 411-419 may be identical to one another to facilitate manufacturability and/or to reduce production costs. That is, axial support structure 400 may consist of a single repeated component that is easy to manufacture in bulk, inspect, replace, and/or the like. This tends to reduce manufacturing and/or operational complexity relative to other types of support structures that include multiple different components. According to some embodiments, rigid links 411-419 may be made of materials that are generally more rigid and/or cheaper than those used in other types of support structures. For example, rigid links 411-419 may be composed of stainless steel instead of a more expensive material such as nitinol. In an alternative embodiment, the axial support structure 400 may not require a high rigidity provided by metals such as stainless steel so rigid links 411-419 may be composed of an even lower cost plastic or thermoplastic materials such as Polyether ether ketone (PEEK), ULTEM, other thermoplastics with high melting points, and/or the like. Particular embodiments of rigid links 411-419 are described in greater detail below with reference to FIGS. 6A-6D.

Adjacent pairs of rigid links 411-419 are rotated by 90 degrees with respect to each other. Consequently, adjacent pairs of pin joints 421-429 pivot about perpendicular axes. This arrangement provides at least two degrees of freedom to axial support structure 400. In this manner, axial support structure 400 may be flexed in any direction.

A channel 430 through axial support structure 400 allows one or more medical instruments to be inserted through axial support structure 400. Additionally or alternately, one or more pull wires, fibers (e.g., optical fibers), cables (e.g., electrical cables), fluids, and/or the like may be inserted into channel 430. As depicted in FIG. 4, channel 430 is enclosed by rigid links 411-419, which serve to reinforce the walls of channel 430. According to some embodiments, reinforcing the walls of channel 430 may protect against pull-through, which occurs when pull wires (and/or other inserted devices) chafe against and eventually pull through the walls of the flexible elongate device.

According to some embodiments, it may be desirable for channel 430 to be wide in order to increase the capacity of channel 430. At the same time, it may be desirable for the outer diameter of the flexible elongate device to be narrow to facilitate insertion into narrow anatomical passageways. To balance the desire for a wide channel 430 and a narrow outer diameter, axial support structure 400 may have thin walls (e.g., 1 mm or less). For example, the walls of axial support structure 400 may be as thin as possible while providing the desired level of axial strength and/or wall reinforcement strength. In comparison, other types of support structures, such as braided support structures, may generally have greater wall thickness than axial support structure 400 due to, for example, overlapping braids.

Axial support structure 400 has a cross-sectional shape that is approximately rectangular. While other types of support structures may be designed to maintain a circular cross section, it is observed that many anatomical passageways are relatively conformable and therefore are capable of accommodating devices with non-circular cross-sections. Accordingly, the rectangular cross-section of axial support structure 400 is not generally regarded as being problematic for many applications. In some applications, the rectangular cross-section of axial support structure 400 is advantageous because the rectangular shape facilitates efficient packing of channel 430. For example, a large circular device (e.g., a medical instrument with a circular cross-section) may occupy the center of channel 430, and one or more smaller devices (e.g., pull wires, optical fibers, and/or electrical cables) may be inserted through unoccupied regions near the four corners of channel 430.

According to some embodiments, axial support structure 400 may be stronger against axial loads than other types of support structures. In particular, the axial strength of axial support structure 400 is provided primarily by rigid links 411-419 while the flexibility is provided primarily by pin joints 421-429. Separating the functionality in this manner allows axial support structure 400 to be constructed without a tradeoff between axial strength and flexibility. By contrast, other types of support structures, such as nitinol flexures, rely on the same features to provide both axial strength and flexibility, resulting in a design tradeoff. For example, increasing the thickness of a nitinol flexure increases axial strength but reduces flexibility, and vice versa.

Advantageously, axial support structure 400 is capable of providing as much axial strength as demanded by a particular application without significantly reducing flexibility. As a result, axial support structure 400 may be suitable for use in an expanded range of applications relative to other types of support structures. For example, axial support structure 400 may be used to support flexible elongate devices with multiple steerable portions, which have more pull wires (and correspondingly greater axial loads) than flexible elongate devices with a single steerable portion. Likewise, axial support structure may be used when an end effector of the flexible elongate device generates axial loads during operation. For example, jaws positioned at the distal end of the flexible elongate device may be actuated using pull wires that generate axial loads on the flexible elongate device.

According to some embodiments, axial support structure 400 may be used to support a relatively stiff elongate device that can be subjected to large axial loads during steering. For example, steering wide and/or thick-walled flexible elongate devices (e.g., a catheter with a larger outer diameter (OD)) may involve greater pulling forces than steering narrower and/or thinner-walled elongate devices. Whereas other types of support structures may have difficulty withstanding the increased axial loads associated with wide and/or thick-walled devices, axial support structure 400 may be well-suited for such applications.

According to some embodiments, axial support structure 400 may be used in applications where mechanical pushing (and/or pulling) is applied to the flexible elongate device. For example, mechanical pushing may be applied to force the flexible elongate device through a narrow constriction in an anatomical passageway and/or to break through a membrane. Consistent with such embodiments, axial support structure 400 may be used to bear the axial loads associated with mechanical pushing and/or pulling.

Figure 5B:
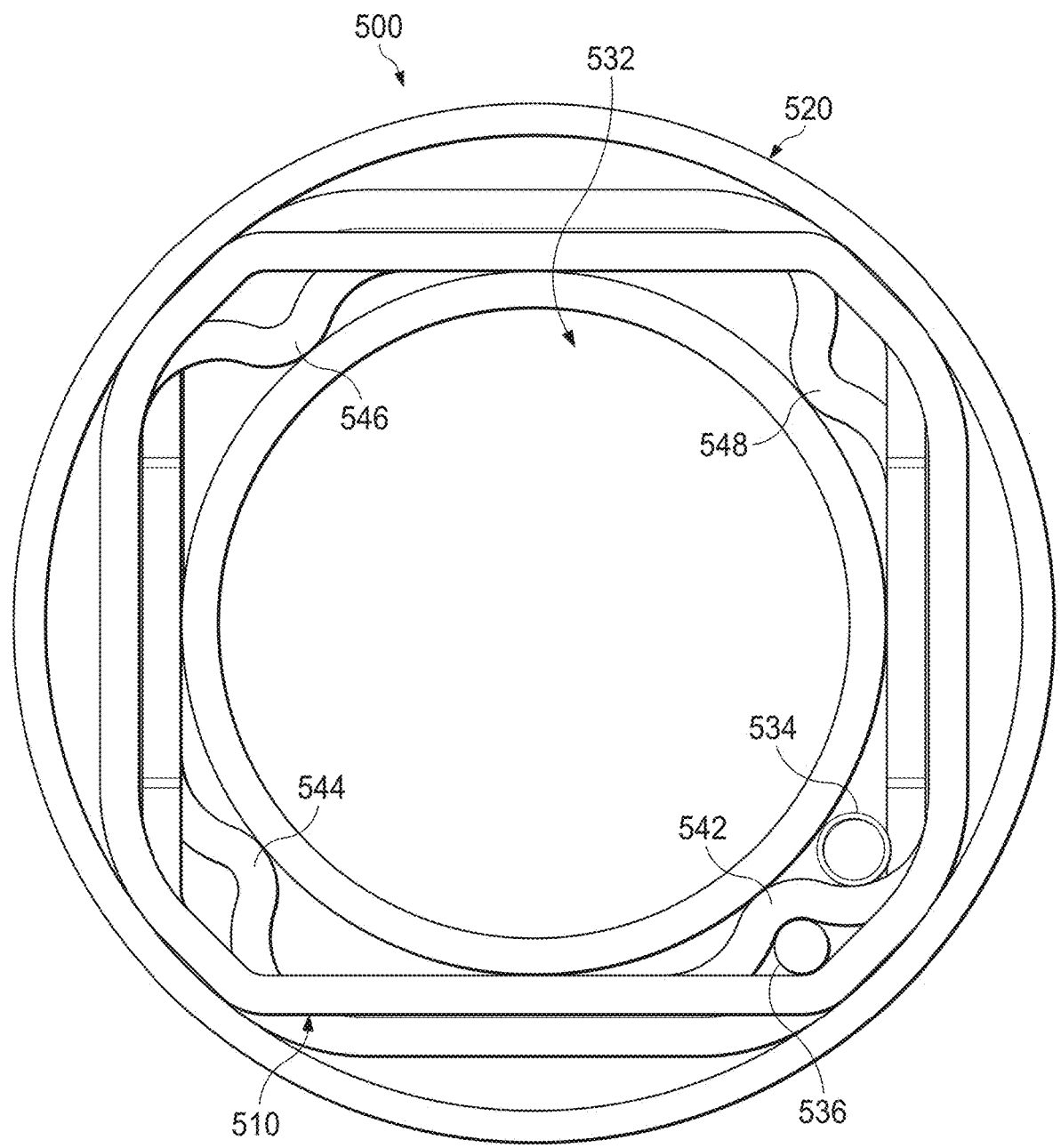

FIGS. 5A and 5B are simplified diagrams of an axially reinforced flexible body 500 according to some embodiments. According to some embodiments consistent with FIGS. 1-4, axially reinforced flexible body 500 may be used to implement one or more sections of a flexible elongate device such as elongate device 202 and/or flexible body 216. In some examples, axially reinforced flexible body 500 may be used to implement a steerable section of a flexible elongate device.

Axially reinforced flexible body 500 includes an axial support structure 510 embedded in a pliable tube 520. According to some embodiments consistent with FIGS. 1-4, axial support structure 510 may be an instance of axial support structure 400. According to some embodiments, pliable tube 520 may be formed using heat shrink tubing. Consistent with such embodiments, although pliable tube 520 is depicted as having a circular cross-section, pliable tube 520 may conform to the shape of axial support structure 510 during heat shrink processing.

One or more lumens are defined through and/or alongside axial support structure 510. As depicted in FIGS. 5A and 5B, a primary lumen 532 occupies a central portion of the channel of axial support structure 510. According to some embodiments, primary lumen 532 may be the largest lumen in axially reinforced flexible body 500. For example, primary lumen 532 may extend to each of the four walls of axial support structure 510. In some examples, primary lumen 532 may be used for the insertion and/or retraction of a medical instrument through axially reinforced flexible body 500. In some examples, primary lumen 532 may accommodate insertion and/or retraction of medical instruments with a circular cross-section.

A secondary lumen 534 and a pull wire lumen 536 extend through portions of the channel of axially reinforced flexible body 500 that are unoccupied by primary lumen 532. Secondary lumen 534 and/or pull wire lumen 536 may be substantially narrower than primary lumen 532. Secondary lumen 534 and/or pull wire lumen 536 may generally occupy corner portions of the channel of axial support structure 510. According to some embodiments, secondary lumen 534 and/or pull wire lumen 536 may be formed by inserting a cable through axially reinforced flexible body 500 prior to performing a heat shrink process and subsequently withdrawing the cable after the heat shrink process to cause a void in pliable tube 520 around secondary lumen 534 and/or pull wire lumen 536. Secondary lumen 534 may be used to insert a small medical instrument, electrical wires, fiber optic cables, and/or the like through axially reinforced flexible body 500. Although a single secondary lumen 534 and a single pull wire lumen 536 are depicted in FIGS. 5A and 5B, it is to be understood that axially reinforced flexible body 500 may include any number of secondary lumens and/or pull wire lumens.

Axial support structure 510 includes a plurality of harnesses 542-548 that form alignment guides running lengthwise through axially reinforced flexible body 500. According to some embodiments, harnesses 542-548 may be formed as push-in strips located in the corners of axial support structure 510. A particular alignment guide is made up of a set of harnesses that are positioned at a same or similar cross-sectional locations along the length of axial support structure 510. According to some embodiments, the set of harnesses may be periodically spaced at fixed intervals axial support structure 510. For example, the fixed interval may include every link, every other link, every fourth link, and/or any other suitable fixed interval. In some examples, the set of harnesses may be spaced by irregular intervals.

According to some embodiments, the alignment guides formed by harnesses 542-548 may be used to align secondary lumen 534 and/or pull wire lumen 536 during formation of the respective lumens (e.g., during the heat shrinking process). For example, as depicted in FIGS. 5A and 5B, secondary lumen 534 extends along the top side of harness 542 and pull wire lumen 536 extends through harness 542. Harnesses 542-548 may reinforce secondary lumen 534 and/or pull wire lumen 536 during operation. For example, harnesses 542-548 may prevent a pull wire inserted into pull wire lumen 536 from pulling through pliable tube 520 into primary lumen 532 and/or secondary lumen 534. Harnesses 542-548 may hold the pull wires in place to maintain steering alignment and/or to prevent the pull wires from drifting during operation, resulting in loss of steering control.

FIGS. 6A-D are simplified diagrams of a rigid link 600 for an axial support structure according to some embodiments. According to some embodiments consistent with FIGS. 1-7, rigid link 600 may be used to implement rigid links 411-419 of axial support structure 400 and/or 510.

Rigid link 600 includes a shaft 610 with a height 'h', a width 'w', a length 'l', and a thickness 't'. According to some embodiments, shaft 610 may be formed from an extruded rectangular tube with a uniform cross-section. In some examples, shaft 610 may be made from stainless steel. In some examples, the height 'h', width 'w', and length 'l' may each be approximately 0.1 inches. In some examples, the thickness 't' may be approximately 0.005 inches. Shaft 610 may optionally include one or more holes 641-649 in various locations for purposes such as allowing heat shrink tubing to bind to shaft 610.

A set (e.g., a pair) of male joint connectors 620 and complementary female joint connectors 630 extend lengthwise from opposite ends of shaft 610. Male joint connectors 620 are affixed to one end of shaft 610 and separated by a height 'h'. Female joint connectors 630 are affixed to the opposite end of shaft 610 and rotated by 90 degrees in relation to male joint connectors 620. Female joint connectors 630 are separated by a width 'w'. Male joint connectors 620 include pins 625 (e.g., convexities protruding from rigid link 600). Female joint connectors 630 include pin receivers 635 (e.g., concavities or holes in rigid link 600).

Male joint connectors 620 and female joint connectors 630 form complementary portions of a pin joint. When a plurality of rigid links are coupled together to form an axial support structure, pins 625 of a first rigid link fit into pin receivers 635 of a second rigid link to form a pivoting pin joint. The range of motion of the pivoting pin joint is determined in part based on how far male joint connectors 620 and/or female joint connectors 630 extend axially (i.e., along an axial direction 660 of rigid link 600) from shaft 610. In some examples, male joint connectors 620 and female joint connectors 630 may extend approximately 0.02 inches lengthwise from the ends of shaft 610.

When 'h' is smaller than 'w', pins 625 are located on the outer surface of rigid link 600 and pin receivers 635 are located on the inner surface of rigid link 600. Conversely, when 'h' is larger than 'w', pins 625 are located on the inner surface of rigid link 600 and pin receivers 635 are located on the outer surface of rigid link 600. In some examples, pins 625 and/or pin receivers 635 may be located on both inner and outer surfaces of rigid link 600 (e.g., pin receivers 635 may include holes that extend from the inner to the outer surface of rigid link 600).

As depicted in FIGS. 6A-D, harnesses 652 and 654 are positioned on opposite corners of shaft 610. According to some embodiments, harnesses 652 and/or 654 may include push-in strips (i.e., strips of shaft 610 that are depressed inwards). According to some embodiments, harnesses 652 and/or 654 may form alignment guides for one or more pull wires. Consistent with such embodiments, harnesses 652 and/or 654 may be used for aligning one or more lumens, such as pull wire lumens, during manufacturing. In some examples, harnesses 652 and/or 654 may be used for maintaining alignment of pull wires during operation and/or for reinforcing pull wire lumens to prevent pull-through into neighboring lumens and/or through the walls of the axial support structure.

Because rigid link 600 includes two harnesses 652 and 654 that are located in opposite corners of shaft 610, an axial support structure constructed using rigid links 600 includes four alignment guides with harnesses alternating between pairs of opposite corners with each link. In some examples, however, rigid link 600 may include any number of harnesses in any location or set of locations. In some examples, rigid link 600 may include four harnesses, one in each corner, so that the alignment guides include harnesses on every link. In some examples, rigid link 600 may include a single harness so that the alignment guides include harnesses every fourth link. In some examples, the harnesses may be centered along the walls of shaft 610 rather than (or in addition to) being located in the corners. In some examples, the harnesses may be located on an outer surface of rigid link 600, such that the alignment guides run along the outside of the axial support structure. In some examples, the harnesses may be shaped as hooks, tubes, ribbons, and/or the like.

When coupling rigid links together to form an axial support structure, adjacent pairs of rigid links are rotated by 90 degrees relative to each other to cause male joint connectors 620 to align with female joint connectors 630 and form a pin joint, such as any of the pin joints 421-429. The height 'h' and the width 'w' of shaft 610 are selected to facilitate alignment between male joint connectors 620 and female joint connectors 630. According to some embodiments, shaft 610 may have an oblong cross-section (i.e., h≠w), such as a rectangular or ellipsoidal cross-section. According to some embodiments, the height 'h' of shaft 610 may be smaller or larger than the width 'w' of the shaft 610 by an amount corresponding to twice the thickness 't' of the walls of shaft 610 (i.e., h=w−2t or h=w+2t). In such embodiments, male joint connectors 620 and female joint connectors 630 may extend straight out along axial direction 660 from shaft 610. On the other hand, in some embodiments, the height 'h' and width 'w' of shaft 610 may be the same and/or otherwise may not be offset from each other by twice the thickness 't'. Consistent with such embodiments, male joint connectors 620 and/or female joint connectors 630 may be shifted relative to the body of shaft 610 (e.g., angled relative to axial direction 660) in order to form a pin joint.

FIG. 7 is a simplified diagram of a method 700 for fabricating an axially reinforced flexible body according to some embodiments. According to some embodiments consistent with FIGS. 1-6, method 700 may be used to fabricate axially reinforced flexible body 500 including an axial support structure, such as axial support structure 400, and/or rigid links, such as rigid link 600. According to some embodiments, method 700 may include fabrication steps that tend to improve the reliability and/or manufacturability of the axially reinforced flexible body, such as laser cutting, laser welding, and/or the like. By contrast, method 700 may avoid fabrication steps that tend to diminish the reliability and/or manufacturability of the axially reinforced flexible body, such as braiding.

At a process 710, a plurality of rigid links are formed. According to some embodiments, the plurality of rigid links may be formed from a rectangular tube, such as an extruded rectangular tube of stainless steel. According to some embodiments, a single rectangular tube with a uniform cross-section is used to form a plurality of rigid links. According to some embodiments, the plurality of rigid links are formed by laser cutting the extruded rectangular tube. The rectangular tube has a height 'h', a width 'w', and a thickness 't', where the height 'h' is smaller or larger than the width 'w' by an amount corresponding to twice the thickness 't'. Each of the plurality of rigid links includes a shaft of length 'l', a set (e.g., a pair) of male joint connectors on an end of the shaft separated by the height 'h', and a set of female joint connectors complementary to the male joint connectors on the opposite end of the shaft separated by the width 'w'. According to some embodiments, a plurality of holes are formed in the plurality of links to facilitate heat shrinking. The plurality of rigid links may be substantially identical to each other to facilitate high manufacturing throughput and/or reliability.

At a process 720, pins are formed on the male joint connectors of the plurality of rigid links. The pins may be welded (e.g., laser welded) onto an inner or outer surface of the male joint connectors. For example, the pins may be welded onto the inner surface when 'h' is larger than 'w' and may be welded onto the outer surface when 'h' is smaller than 'w'.

At a process 730, pin receivers are formed on the female joint connectors of the plurality of rigid links. According to some embodiments, the pin receivers may include holes that extend from the inner to the outer surface of the female joint connectors, where the holes are sufficiently large to accommodate the pins. According to some embodiments, the pin receivers may include recessions in the inner or outer surface of the female joint connectors. The pin receivers may be formed by laser cutting.

At a process 740, one or more harnesses are formed on the plurality of rigid links. The harnesses may be formed on one or more corners of the shaft of the rigid links (and/or may be centered lengthwise along the shaft). For example, each rigid link may include two harnesses located on opposite corners of the shaft. According to some embodiments, each harness may be formed by cutting (e.g., laser cutting) slits in the shaft and pushing in the portion of the shaft between the slits. For example the slits may include a pair of parallel slits. The pushed in portion of the shaft juts into the channel of the axial support structure to form an alignment guide inside the channel.

At a process 750, the plurality of rigid links are coupled to form an axial support structure. Each of the plurality of rigid links is rotated by 90 degrees with respect to adjacent rigid links so as to align the male joint connectors and the female joint connectors of the adjacent rigid links. The pins of the male joint connectors are inserted into the pin receivers of the female joint connectors to form pin joints, where each pin joint pivots around an axis perpendicular to the axial direction of the axial support structure. The plurality of rigid links may snap together to form the pin joints. The axial support structure may include three or more rigid links (three rigid links couple to form two perpendicular pin joints, allowing the axial support structure to flex in any direction).

At a process 760, the axial support structure is encapsulated in a pliable tube to form an axially reinforced flexible body. According to some embodiments, the pliable tube may be a plastic and/or rubber tube that is disposed around the axial support structure by heat shrinking. According to some embodiments, one or more cables may be inserted through the axial support structure prior to heat shrinking so that the pliable tube forms one or more lumens around the one or more cables during the heat shrinking process. For example, one or more cables may be inserted at a location where a secondary lumen and/or a pull wire lumen is desired. The pliable tube may conform to the shape of the axial support structure, resulting in axially reinforced flexible body having approximately the same rectangular cross-section as the axial support structure.

In an alternative embodiment, it may be desirable to provide a jacket over the axial support structure that will provide protection and some axial reinforcement but still maximize flexibility of the axial support structure. Thus according to some embodiments, one or more layers may be formed between the axial support structure and the pliable tube preventing the pliable tube from melting and entering gaps in the axial support structure during a heat shrink process. The one or more layers may be formed from a material with a high melting point such as polytetrafluoroethylene (PTFE). A pliable tube may be disposed around the plurality of layers by heat shrinking and conform to the axial support structure providing protection to the axial support structure as well as some axial support resulting in an axially reinforced flexible body having approximately the same rectangular cross-section as the axial support structure. However, since the pliable tube does not melt within gaps of the axial support structure, bending flexibility is maintained. Additional embodiments providing for various layers within a flexible elongate device with an axial support structure is disclosed in U.S. Patent Application No. 62/535,673 (filed Jul. 21, 2017) (titled "Flexible Elongate Devices and Methods") which is incorporated by reference herein in its entirety.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An axial support structure for a flexible elongate device comprising:
    a plurality of rigid links coupled by pin joints, wherein:
        each of the plurality of rigid links comprises a shaft, a pair of male joint connectors each comprising a male tab coplanar with the shaft and extending axially from a first end of the shaft, and a pair of female joint connectors each comprising a female tab coplanar with the shaft and extending axially from a second end of the shaft opposite the first end, the female joint connectors being complementary to the male joint connectors and being rotated by 90 degrees relative to the male joint connectors, wherein each of the male joint connectors includes a pin extending from the male tab in a direction perpendicular to an axial direction of the shaft and each female tab defines an aperture; and each of the plurality of rigid links is rotated by 90 degrees with respect to neighboring links among the plurality of rigid links, thereby aligning each pair of male joint connectors with a neighboring pair of female joint connectors to form the pin joints in which each aperture encircles a corresponding pin.

2. The axial support structure of claim 1, wherein:
the pin joints pivot around an axis perpendicular to an axial direction of the flexible elongate device.

3. The axial support structure of claim 1, wherein the plurality of rigid links are substantially identical to each other.

4. The axial support structure of claim 1, wherein the plurality of rigid links are composed of stainless steel or plastic.

5. The axial support structure of claim 1, wherein the shaft has a rectangular cross-section.

6. The axial support structure of claim 1, wherein the shaft has a width, a height, a length, and a thickness, and wherein the pair of male joint connectors are separated by the height and the pair of female joint connectors are separated by the width.

7. The axial support structure of claim 6, wherein the width and the height are related according an equation $w=h+2t$ or an equation $w=h-2t$, where w represents the width, h represents the height, and t represents the thickness.

8. The axial support structure of claim 1, wherein each of the plurality of rigid links further comprises one or more harnesses.

9. The axial support structure of claim 8, wherein each of the one or more harnesses includes push-in strips on the shaft.

10. The axial support structure of claim 8, wherein at least one of the one or more harnesses are located in a corner of the shaft.

11. The axial support structure of claim 8, wherein the one or more harnesses have a shape selected from one or more of a strip, a hook, and a tube.

12. The axial support structure of claim 8, wherein the one or more harnesses form an alignment guide for one or more pull wires inserted into the axial support structure.

* * * * *